United States Patent [19]
Graves et al.

[11] Patent Number: 6,088,087
[45] Date of Patent: Jul. 11, 2000

[54] TRANSCUTANEOUS MEASUREMENT OF SUBSTANCE IN BODY TISSUES OR FLUID

[75] Inventors: Pierre Robert Graves; Jane Allison Graves, both of Abingdon, United Kingdom

[73] Assignee: Ramam Technical Research Ltd., Bicester, United Kingdom

[21] Appl. No.: 09/079,320

[22] Filed: May 15, 1998

[30] Foreign Application Priority Data

Nov. 17, 1995 [GB] United Kingdom .................. 9523524

[51] Int. Cl.⁷ .................................................. G01N 33/48
[52] U.S. Cl. ............................................. 356/39; 600/473
[58] Field of Search ........................... 356/39, 305, 302; 600/315, 316, 322, 368, 473

[56] References Cited

U.S. PATENT DOCUMENTS

| | | | |
|---|---|---|---|
| 4,029,085 | 6/1977 | DeWitt et al. | 128/2 R |
| 5,172,693 | 12/1992 | Doody | 128/633 |
| 5,379,764 | 1/1995 | Barnes et al. | 356/39 |
| 5,672,875 | 9/1997 | Block et al. | 356/39 |
| 5,791,345 | 8/1998 | Ishihara et al. | 356/39 |
| 5,792,050 | 8/1998 | Alam et al. | 356/39 |

FOREIGN PATENT DOCUMENTS

| | | |
|---|---|---|
| 0 160 768 A1 | 11/1985 | European Pat. Off. . |
| 0 623 306 A1 | 11/1994 | European Pat. Off. . |
| 0 641 542 A2 | 3/1995 | European Pat. Off. . |
| 0 714 628 A1 | 6/1996 | European Pat. Off. . |
| 2 022 244 | 12/1979 | United Kingdom . |
| 2 235 288 | 2/1991 | United Kingdom . |

*Primary Examiner*—Robert H. Kim
*Assistant Examiner*—Tu T. Nguyen
*Attorney, Agent, or Firm*—Roberts Abokhair & Mardula, LLC

[57] ABSTRACT

An apparatus and method for transcutaneous measurement of a substance within a body. Transcutaneous measurement of substances within a subjects' tissues or fluids is effected through the use of the present invention. A light source, focused by an optical system, directs light towards a subject. Light returning from the subject as a result of this illumination, is collected, focused and directed to a detection system. The output of this detection system can then be analyzed to determine the concentration of the substance being measured. In a preferred embodiment bilirubin is measured. However, the measurement of substances such as oxygen, carbon dioxide, glucose, albumin, hemoglobin and cholesterol, among others, is also contemplated.

26 Claims, 2 Drawing Sheets

TRANSCUTANEOUS MEASUREMENT OF SUBSTANCE IN BODY TISSUES OR FLUID

RELATIONSHIP TO OTHER APPLICATIONS

This application is based upon application No. PCT/GB96/02823, filed on Nov. 15, 1996 and Great Britain application, priority No. 95/23524.8, filed on Nov. 17, 1995.

FIELD OF THE INVENTION

This invention relates generally to an apparatus for use in the transcutaneous measurement of a given substance within body tissues or fluids of a subject and to a method of carrying out said measurement.

BACKGROUND

Measurement of substances within body tissues or fluids, such as blood, are commonly carried out for use in diagnosis or in the monitoring of certain medical conditions. In many cases, such as in the measurement of bilirubin in blood serum, a blood sample is taken for analysis. This is commonly done in the assessment of jaundice in new-born babies by taking a blood sample from the baby's heel. However, this procedure can traumatize the baby, can lead to infection (particularly if repeated samples need to be taken to monitor treatment) and does not provide a reliable measurement at high concentrations of bilirubin.

A number of non-invasive optical techniques have been proposed for measurement of substances such as bilirubin. These involve illuminating the subject's skin with one or more wavelengths of light, detecting the light reflected from the skin, or in some cases transmitted through the body tissues, e.g. through a finger, and analyzing the results to measure a spectral characteristic of the reflected or transmitted light caused by the substance to be measured. Such measurements are, however, subject to interference by a number of factors including: skin pigmentation, maturity, the effects of treatment such as phototherapy and the presence of other substances such as blood hemoglobin. In an attempt to overcome these difficulties, complex analyses, usually of several wavelengths, are carried out to try to reduce the effect of the interferences on the desired measurement.

The present invention aims to avoid or significantly reduce such problems.

SUMMARY OF THE INVENTION

According to a first aspect of the invention, there is provided an apparatus for use in the transcutaneous measurement of a given substance in body tissues or fluids of a subject having a light source for directing light towards the subject; a light detection means; and an optical system which has a focusing means for focusing light returning from the subject and optical selecting means through which light from said focusing means is passed, arranged such that only light returning from an area at a selected level beneath or on the surface of the subject is transmitted to the detection means.

According to a second aspect of the invention, there is provided a method for transcutaneous measurement of a given substance in body tissues or fluids of a subject in which light is directed towards the subject and light returning from the subject, as a result of such illumination, is focused and passed through an optical selecting means such that only light returning from an area at a selected level beneath or on the surface of the subject is detected.

One particular embodiment of the invention provides apparatus and a method of measuring bilirubin and, in a preferred arrangement, the apparatus detects a fluorescent emission stimulated by the illumination.

Other features of the invention will be apparent from the following description and from the subsidiary claims of the specification.

It should be noted that the term measurement is used to include a measurement sufficient only to identify the presence of a given substance as well as quantitative and semi-quantitative measurements.

BRIEF DESCRIPTION OF THE DRAWINGS

The invention will now be further described, merely by way of example, with reference to the accompanying drawings in which.

DETAILED DESCRIPTION OF THE DRAWINGS

Figure 1:
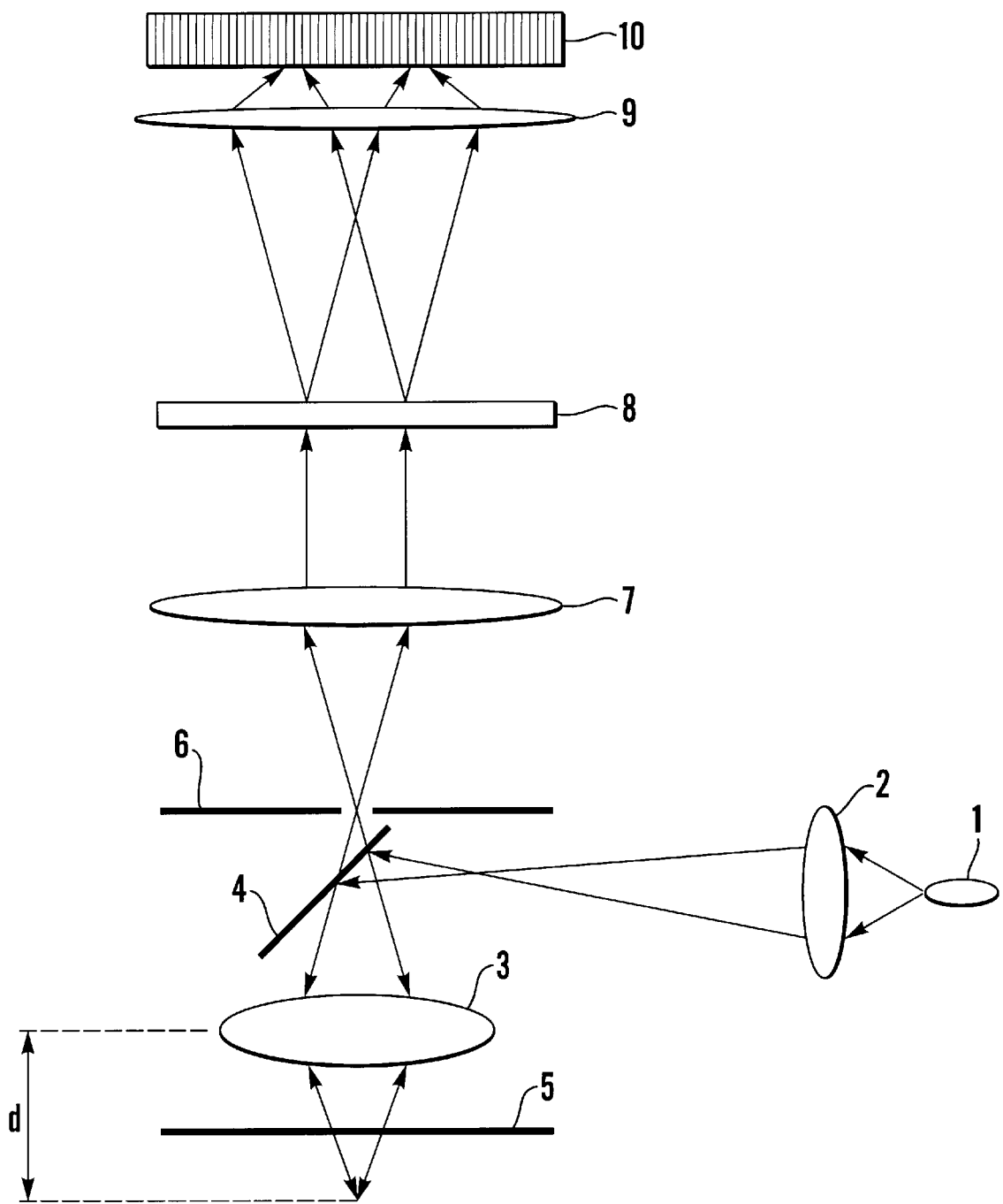
FIG. 1 shows a schematic diagram of apparatus according to one embodiment of the invention.

FIG. 1 shows a schematic diagram of the apparatus of the present invention. The light emitted from light source 1, such as a light emitting diode or laser diode, is focused by means of an optical system comprising first lens 2, second lens 3 and beamsplitter 4. In a preferred embodiment, beamsplitter 4 is a semi-silvered mirror directed towards a subject. As shown, the light passes through skin 5 of the subject and is focused at a point a selected distance d from second lens 3 beneath the surface of skin 5.

Light returning from the illuminated point is collected and focused by lens 3 through beamsplitter 4 and through spatial filter 6. As illustrated, spatial filter 6 is in the form of a pinhole and, as shown, the optical arrangement is such that only light returning from the illuminated point at the distance d from second lens 3 is focused on and thus able to pass through the pinhole. Light passing through the pinhole is then directed to a detection system comprising third lens 7 which collimates the light, a frequency selecting or dispersing element 8 such as a graduated filter or a transmission grating which acts to separate the component wavelengths of the returning light, and fourth lens 9 which focuses the separated wavelengths onto detection means 10. In a preferred embodiment, detection means 10 is in the form of a multi-channel detector such as a photodiode array or charged coupled device. In alternative embodiments a reflection grating may be used as dispersing element 8.

An output of detection means 10 representing intensity values for wavelengths detected by the respective detector elements can be analyzed, e.g. by maximum entropy or maximum likelihood computations to provide an optimized and least biased measurement of the concentration of the substance being measured.

It will be appreciated that by arranging the optical detection system so that only light returning from an area at a given distance beneath the skin is detected, a true, transcutaneous measurement is enabled. By this means, interference due to skin pigmentation, which is present at or near the surface of the skin, can be avoided by taking measurements from an area beneath the pigment layer.

The ability to select the level of the area from which measurements are taken also helps overcome problems due to treatment by phototherapy which tends to rapidly reduce bilirubin levels in the skin tissue even though levels in the blood serum may still be high. An initial screening may thus take measurements from high in the dermis but later measurements may need to be taken from lower in the dermis or in the subcutaneous fat. The level from which measurements are taken is selected by adjustment of the optical system, e.g. by axial adjustment of one or more of the lenses and/or of spatial filter 6.

Maturity of the skin also affects measurements as the thickness of skin can vary considerably with age, particularly for pre-term babies. The apparatus described thus enables the measurements to be taken from the appropriate level whatever the thickness of the skin.

Also, by taking measurements from a selected area in which the substance being measured is concentrated, interference due to the presence of other substances can be reduced. The spatial filtering thus enables the user to select the level or layer of skin, tissue or body fluid vessel from which measurements are made. Measurement may be taken from areas which are several millimeters or more beneath the surface of the skin or in some cases, from the skin surface itself. Depending on the optics used, the area from which measurements are made can be reduced to a size approximately 20 microns in diameter and 20 microns in depth.

The method described thus provides a significant advantage over the prior art which only measures light reflected from the surface of the skin, or an average of reflectance from several different layers of the skin. Similarly, transmission techniques only provide an average measurement for the tissues and fluids through which the light is transmitted.

A pinhole provides a simple but effective spatial filter as described above as only light emanating from the selected area is able to pass through the pinhole; light from other areas is focused by second lens 3 away from the pinhole and so is unable to pass through the pinhole. By this means, light from other areas is rejected by the optical selection system.

It should be noted that the term pinhole is used to cover actual pinholes and their equivalent, e.g. a small hole made by other means, or a small transparent area within an opaque area.

It will be appreciated that other forms of a spatial filter can be used in place of or in addition to a pinhole. It is also possible to move second lens 3 axially and thus to detect spectral images of several difference levels or slices within the subject. Such images can then be processed to construct a 3-dimensional image of the area by means of tomography. A further possibility would be to use a liquid crystal light valve, e.g. arranged to simulate a pinhole or arranged to transmit only a cone of light focused from the selected level. The provision of a spatial filter also means that only a single light source, rather than a plurality or light sources of difference wavelengths, need be used.

The method described in general terms above will now be described in more detail with reference to the measurement of bilirubin.

Bilirubin is a large molecule with certain groups of atoms (chromophores) which absorb blue light and emit a longer wavelength light, by fluorescence, giving a characteristic yellow-orange color. Babies with jaundice have this yellow/orange color due to the solubility of bilirubin in skin tissues, especially in fat. The red color of blood is caused by hemoglobin which also absorbs light in the blue part of the spectrum and so interferes with measurements based on the absorption or reflection of light.

The presence of bilirubin can be detected by either measuring its absorbance or its fluorescence. The former can be detected by eye but is notoriously inaccurate and becomes impossible once phototherapy has started. As mentioned above, various skin reflectometers have been proposed to provide a more accurate measurement of skin color due to bilirubin but these suffer from the problems caused by the various interfering factors discussed above and it is believed that it is these difficulties which have so far prevented an accurate and reliable noninvasive measurement system from being produced.

The method described herein overcomes or reduces these difficulties by the use of spatial filtering, as described above, to select the layer of skin from which measurements are taken. In addition, when measuring bilirubin, its fluorescence emission is preferably detected in addition to or in place of diffusely reflected light. Furthermore, as will be described in more detail below, analysis of the spectral data obtained is undertaken by statistically optimized data processing software to overcome the remaining interference factors.

The apparatus used for measuring bilirubin uses a blue light emitting diode (LED) which provides a light source closely approximating an ideal point source. Such a diode has a peak output wavelength of 470 nm, which corresponds exactly with the absorption maximum of bilirubin molecules and so requires no filters. It can also be powered by a small battery.

For screening for the presence of bilirubin, the optical system comprising first lens 2, second lens 3 and beamsplitter 4 is arranged to focus light from the LED in a layer of fat approximately 600 microns beneath the surface of the skin, which is the region where the bilirubin concentration is the highest.

Backscattered fluorescent light and diffusely reflected light from the skin is collected by second lens 3 and passes through beamsplitter 4 to spatial filter 6 which acts to block light coming from anywhere other than the focus of second lens 3. Only light emanating from the region 600 microns beneath the surface of the skin where second lens 3 is focused is thus transmitted through spatial filter 6. Light scattering by melanin pigments which cause skin color occurs in the epidermis closer to the skin surface and is thus excluded from the measurement.

The light passing through spatial filter 6 is collimated by third lens 7 and then dispersed by dispersing element 8, such as transmission grating. An inexpensive plastics grating film having more than 900 grooves per millimeter has been found to provide excellent dispersion of the component wavelengths. Dispersing element 8 thus performs true spectroscopy rather than analyzing just one or two wavelengths. The output of dispersing element 8 is focused by proximity lens 9 onto detector 10, such as a photodiode array. Detector 10 may, for example, comprise a linear array of 256 elements. The wavelengths emerging from dispersing element 8 at different angles are each focused on a respective element of detector 10 so the outputs from the individual elements of the detector provide a measurement of the intensity of the various wavelengths.

Figure 2:
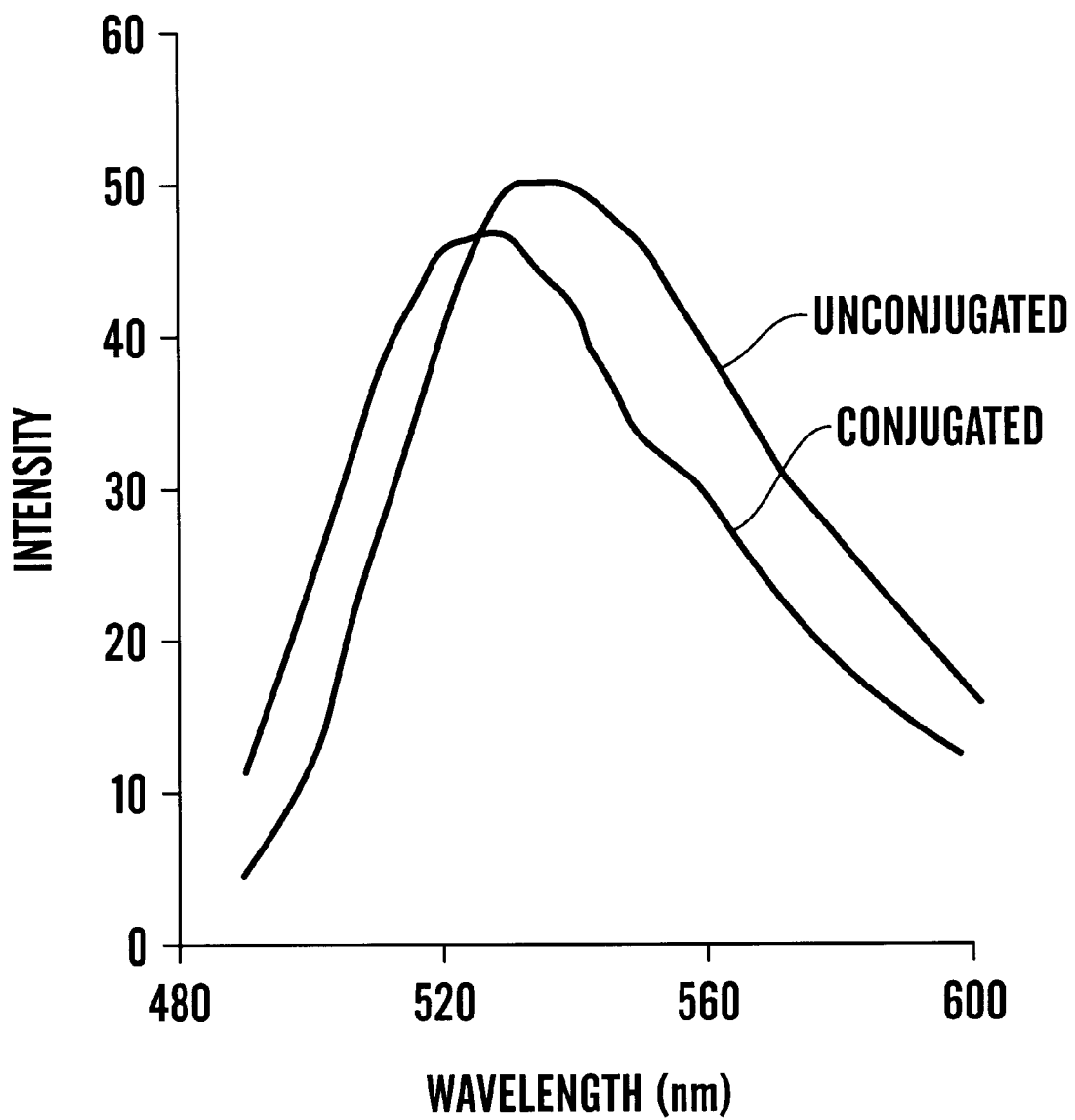
FIG. 2 is a graph illustrating the optical emission spectrum for an aqueous solution of bilirubin.

FIG. 2 show typical spectral emission curves for bilirubin. As shown, visible fluorescence can be detected from both conjugated bilirubin 202 and unconjugated bilirubin 204, although the spectral bands are rather broad and overlap substantially.

The outputs of detector 10 are preferably analyzed by microprocessor data reduction techniques to improve specificity, accuracy and reliability. Two particular statistical approaches are favored: a maximum likelihood method and a factor analysis. Further information on these techniques can be found in a book by D. J. Gardiner and P. R. Graves entitled Practical Raman Spectroscopy, Chapter 4, published by Springer-Verlag in 1989 (ISBN 3-540-50254-8) and other references given therein. The maximum likelihood method (also known as the maximum entropy method) performs a Fourier reconstruction of the spectral data subject to the constraints of (i) maximizing the entropy content of the solution and (ii) minimizing the difference between the sum of component functions of the solution and the spectral dataset. The second approach, that of factor analysis, relies on a least-squares optimization of known component functions (such as the fluorescence curves for bilirubin and the absorbance curve for melanin). The number of functions fitted and the reliability of the solution obtained is optimized through reference to the auto-correlation matrix for the set of component functions.

By analyzing the complete spectral information, it is possible to significantly reduce interferences due to the presence of other substances. With appropriate optimization of the apparatus and analysis techniques it is possible to distinguish between the conjugated and unconjugated forms of bilirubin.

The apparatus described above thus enables a compact, hand-held microprocessor controlled unit to be provided for use by doctors, nurses and other medical staff. Such a unit enables rapid, noninvasive measurement of bilirubin levels to be carried out for use in diagnosis, screening and monitoring of jaundice.

A more detailed description has been given in relation to apparatus for measuring bilirubin but it will be appreciated that other substances, such as oxygen, carbon dioxide, glucose, albumen, hemoglobin and cholesterol, can be measured by similar apparatus.

It will also be appreciated that other light sources can be used in place of the LED or laser diodes referred to above, although the light source should preferably approximate to an ideal point source to enable spatial filtering to be carried out as described above. The light source is preferably focused on the selected area but diffuse illumination of the subject is also possible. If the light source emits a very narrow, collimated beam, beamsplitter 4 can be replaced by a small mirror which would provide only a small obstruction to light returning from second lens 3 to spatial filter 6.

Other forms of frequency selecting or dispersing elements can also be used, such as a variable filter.

A monolithic multi-channel detector is preferably used rather than a plurality of individual photodiodes. However, a position sensitive detector or other form of detector capable of providing an output indicative of the relevant wavelength(s) sensed can also be used.

Although complete spectral analysis, e.g. of 128 or 256 wavelengths or wavelength bands, is preferably carried out it may, in some circumstances, only be necessary to detect certain specific wavelengths which are found to be characteristic of the substance being measured. In some cases, a measurement of, say, three of four wavelengths may be sufficient to identify a particular substance and, if the substance emits a very characteristic or particularly strong signal, it may only be necessary to detect a single wavelength. In general, for simple least-squares optimism, it is necessary to have one more datapoint than the number of components one is trying to distinguish between. Thus, in theory, at least six datapoints would be required to distinguish between the components of a five component system.

Preferred and alternate embodiments of the present invention have now been described in detail. It is to be noted, however, that these embodiments are merely illustrative of the principles underlying the inventive concept of the present invention. It is therefore contemplated that various modifications of the disclosed embodiments will be apparent to persons of ordinary skill in the art, without departing from the scope of the present invention.

What is claimed is:

1. An apparatus for use in transcutaneous measurement of a substance comprising:
   a light source for directing light towards a subject;
   a light detection means for detecting at least one selected wavelength or wavelength band; and
   an optical system, the optical system comprising:
      a focusing means for collecting and focusing divergent light emanating from the subject; and
      an optical selecting means, that is positioned, in use, relative to the said focusing means such that light from the focusing means passes through the optical selecting means, and such that light returning from a pre-selected region only of the subject is able to pass through the optical selecting means to the light detection means, the said pre-selected region of the subject being one of the following:
   (I) at a pre-selected distance beneath the surface of the subject;
   (II) pre-selected to be on the surface of the subject; whereby the intensity of light at the at least one selected wavelength or wavelength band returning from the selected region can be determined.

2. The apparatus of claim 1 where the light source approximates to an ideal point source.

3. The apparatus of claim 2 where the light source comprises a light emitting diode.

4. The apparatus of claim 2 where the light source comprises a laser diode.

5. The apparatus of claim 1 where the light detection means is arranged to carry out spectral analysis of the light received.

6. The apparatus of claim 1 where the light detection means comprises frequency selecting means.

7. The apparatus of claim 1 where the light detection means comprises frequency dispersing means.

8. The apparatus of claim 7 where the light detection means comprises a transmission grating for dispersing light of different frequencies.

9. The apparatus of claim 7 where the light detection means comprises a reflection grating for dispersing light of different frequencies.

10. The apparatus of claim 1 where the detection means comprises a multi-channel detector.

11. The apparatus of claim 1 further comprising:
    analysis means for analyzing an output of the light detection means.

12. The apparatus of claim 11 where the analysis means comprises software which applies at least one predetermined algorithm to the output of the light detection means to identify a spectral information characteristic of the given substance.

13. The apparatus of claim 11 where the analysis means comprises firmware which applies at least one predetermined algorithm to the output of the light detection means to identify a spectral information characteristic of the given substance.

14. The apparatus of claim 1 where the optical selecting means comprises a spatial filter.

15. The apparatus of claim 14 where the spatial filter comprises a pin hole.

16. The apparatus of claim 1 where the optical system comprises means for focusing light from the light source on the selected region at the selected distance beneath the surface of the subject's skin.

17. The apparatus of claim 16 where the optical system comprises a lens which acts to focus light at the selected distance beneath the subject's skin and receive light returning therefrom.

18. An apparatus for use in transcutaneous measurement of a substance comprising:

a light source for directing light towards a subject;

a light detection means for detecting at least one selected wavelength or wavelength band; and an optical system, the optical system comprising:

a focusing means for collecting and focusing divergent light emanating from the subject; and an optical selecting means, where the light from the focusing means passes through the optical selecting means and is arranged such that only light returning from a selected region which is at a selected distance beneath the subject's skin is transmitted to the light detection means, the selected distance being determined by adjustment of the optical system, and where the intensity of light at the at least one selected wavelength or wavelength band returning from the selected region can be determined.

19. The apparatus of claim 18 where the adjustment is effected by axial movement of at least one component of the optical system.

20. The apparatus of claim 1 where the optical system is arranged so that the region has a diameter of 20 microns or less and a depth of 20 microns or less.

21. The apparatus of claim 1 where the optical system is arranged so that the region is at least several millimeters beneath the surface of the subject's skin.

22. The apparatus of claim 1, where the apparatus is arranged to detect light emitted by fluorescence from the subject resulting from illumination by the said light source.

23. The apparatus of claim 1, where the apparatus is arranged to provide a measurement of the presence of bilirubin in the subject.

24. The apparatus of claim 23 where the light source emits light having a wavelength of approximately 470 nm.

25. The apparatus of claim 1, where the apparatus is a compact, hand-held unit.

26. A method for transcutaneous measurement of a substance within a subject comprising:

directing light towards the subject;

collecting divergent light that emanates from the subject as a result of directing the light toward the subject;

focusing the collected divergent light;

passing the focused light though an optical selecting means; that is positioned relative to the said focusing means such that light returning from a pre-selected region only of the subject passes through the optical selecting means to the light detection means the said pre-selected region being one of the following:

(I) at a pre-selected distance beneath the surface of the subject;

(II) pre-selected to be on the surface of the subject; and determining the intensity of light at one or more selected wavelength or wavelength bands returning from the pre-selected region.

* * * * *